US009185911B2

(12) United States Patent
Inami et al.

(10) Patent No.: US 9,185,911 B2
(45) Date of Patent: Nov. 17, 2015

(54) COMPOSITION FOR PREVENTING PLANT DISEASES AND METHOD FOR PREVENTING THE DISEASES

(75) Inventors: Syunichi Inami, Mobara (JP); Yuji Yanase, Mobara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 596 days.

(21) Appl. No.: 11/883,352

(22) PCT Filed: Jan. 20, 2006

(86) PCT No.: PCT/JP2006/300890
§ 371 (c)(1),
(2), (4) Date: Jul. 31, 2007

(87) PCT Pub. No.: WO2006/082723
PCT Pub. Date: Aug. 10, 2006

(65) Prior Publication Data
US 2008/0312184 A1    Dec. 18, 2008

(30) Foreign Application Priority Data

Feb. 4, 2005 (JP) ................................. 2005-029312
Feb. 4, 2005 (JP) ................................. 2005-029313

(51) Int. Cl.
*A01N 43/56*    (2006.01)
*A01N 43/653*   (2006.01)
*A01N 55/10*    (2006.01)
*A01N 43/54*    (2006.01)

(52) U.S. Cl.
CPC ............... *A01N 43/54* (2013.01); *A01N 43/56* (2013.01)

(58) Field of Classification Search
None
See application file for complete search history.

(56) References Cited

U.S. PATENT DOCUMENTS

| 5,747,518 A | 5/1998 | Yoshikawa et al. | |
|---|---|---|---|
| 2005/0101639 A1* | 5/2005 | Ammermann et al. | 514/345 |
| 2008/0113979 A1 | 5/2008 | Foor | |
| 2008/0269051 A1 | 10/2008 | Suty-Heinze et al. | |

FOREIGN PATENT DOCUMENTS

| EP | 0737682 A1 | 10/1996 |
|---|---|---|
| JP | 09-235282 A | 9/1997 |
| JP | 09-301974 A | 11/1997 |
| JP | 11-302107 A | 11/1999 |
| JP | 11-302108 A | 11/1999 |
| JP | 11-302110 A | 11/1999 |
| JP | 11-302111 A | 11/1999 |
| JP | 2001-072510 A | 3/2001 |
| JP | 2001-072511 A | 3/2001 |
| JP | 2001-072512 A | 3/2001 |
| JP | 2001-072513 A | 3/2001 |
| WO | WO 2006/036827 A1 | 4/2006 |
| WO | WO 2006/040123 A2 | 4/2006 |

OTHER PUBLICATIONS alanwood.net fungicide list, 2002, retrieved from the internet on Sep. 9, 2010, URL: http://web.archive.org/web/20020625095743/http://www.alanwood.net/pesticides/class_fungicides.html.*
English language translation of JP 2001-072510.
English language translation of JP 09-301974.
English language translation of JP 2001-072511.
English language translation of JP 2001-072512.
English language translation of JP 2001-072513.
English language translation of JP 11-302107.
English language translation of JP 11-302108.
English language translation of JP 11-302110.
English language translation of JP 11-302111.
Office Action, Japanese Application No. 2007-501528, dated Jun. 1, 2010.
Extended European Search Report dated Sep. 25, 2012 issued in EP 11 19 6112.
Dave W. Bartett et al.: "Understanding the strobilurin fungicides", Pesticide Outlook vol. 12, No. 4, Nov. 6, 2001, pp. 143-148.
Office Action issued by the Brazilian Patent Office in corresponding Brazilian Patent Application No. BR122014017874-3 on May 20, 2015 (8 pages including partial English translation).

* cited by examiner

*Primary Examiner* — San-Ming Hui
*Assistant Examiner* — Andrew Lee
(74) *Attorney, Agent, or Firm* — Buchanan, Ingersoll & Rooney PC

(57) ABSTRACT

The present invention is to provide a composition for preventing plant diseases which comprises at least Component I and Component II, is capable of obtaining a synergic effect that cannot be expected with each single component, is capable of markedly increasing a control effect in a much smaller amount of chemicals against various plant pathogens, and causes no phytotoxicity suffering.
A composition for preventing plant diseases comprises Components I and II as active ingredients. The Component I is (RS)—N-[2-(1,3-dimethylbutyl)thiophen-3-yl]-1-methyl-3-tri fluoromethyl-1H-pyrazole-4-carboxamide. As the Component II, there can be exemplified, for example, tetraconazole, flutriafol, imibenconazole, triadimefon, simeconazole, oxpoconazole fumarate, prothioconazole, bupirimate, spiroxamine, metiram, dodine, anilazine, chlozolinate, oxycarboxin, ethaboxam, iprovalicarb, pyrazophos, fluoroimide, diflumetorim, fenhexamid, famoxadone, fenamidone, cyazofamid, zoxamide, cyflufenamid, boscalid, benthiavalicarb-isopropyl, picoxystrobin, pyraclostrobin, fluoxastrobin or dimoxystrobin.

2 Claims, No Drawings

COMPOSITION FOR PREVENTING PLANT DISEASES AND METHOD FOR PREVENTING THE DISEASES

TECHNICAL FIELD

The present invention relates to a composition for preventing plant diseases comprising at least two or more kinds of active ingredients and having a synergic control effect against plant diseases such as gray mold, powdery mildew, *Sclerotinia* rot, *Alternaria* leaf spot, diseases caused by *Rhizoctonia* and the like, and a method for preventing plant diseases.

BACKGROUND ART

From the past, a large number of chemical fungicides have been used. However, it has become obvious that there is a problem of resistance of plant pathogens against chemical active ingredients associated with frequent use or overdose of such chemical active ingredients with the same action having a similar skeleton for controlling diseases of the same kind.

On the other hand, in late years, consumer's needs for crops with reduced agricultural chemicals or social needs for reduced environmental burdens of chemical pesticides.

Furthermore, in a farm field where chemicals are actually used, when two or more kinds of chemicals are mixed together using a tank mixing method for the treatment, active ingredients which are incompatible with each other are combined, causing lots of risks such as reduced effects of each active ingredients or phytotoxicity suffering to the plants.

Under these circumstances, compositions for preventing plant diseases with significant effect against fungi resistant to the existing active ingredients and with great effect even in a much smaller amount of an active ingredient have been in demand. Furthermore, in order to prevent plant pathogens from having chemical resistance as well, there have been demanded a composition for preventing plant diseases with good compatibility comprising components (compounds) with different actions having different basic skeletons, and a method for preventing the plant diseases.

In JP Patent Publication No. 1997-235282A and European Patent Publication No. 737682 is disclosed
(RS)—N-[2-(1,3-dimethylbutyl)thiophen-3-yl]-1-methyl-3-tri fluoromethyl-1H-pyrazole-4-carboxamide (a common name: penthiopyrad (currently applied for ISO), hereinafter referred to as penthiopyrad) which has a control effect against various diseases.

[Patent Document 1] JP Patent Publication No. 1997-235282A

[Patent Document 2] European Patent Publication No. 737682 (EP0737682)

DISCLOSURE OF THE INVENTION

It is the object of the present inventors to provide a composition for preventing plant diseases with significant effect against fungi having resistance to the existing active ingredients and a composition for preventing plant diseases having high activity even in a small amount of an active ingredient to be given to habitation environment of plant pathogens.

The present inventors had conducted a study on the combination of penthiopyrad and other fungicide components and as a result, had found that by combining penthiopyrad and specific fungicide components, a synergic control effect which was not expected with a single component against various plant pathogens could be obtained and no phytotoxicity suffering to plants were caused. Thus, the present invention had been completed.

That is, the present invention relates to a composition for preventing plant diseases and a method for preventing the diseases as specified by the following maters.

[1] A composition for preventing plant diseases comprising Components I and II as active ingredients, wherein the Component I is RS)—N-[2-(1,3-dimethylbutyl)thiophen-3-yl]-1-methyl-3-tri fluoromethyl-1H-pyrazole-4-carboxamide, and the Component II is one or more compounds selected from a group consisting of tetraconazole, flutriafol, imibenconazole, triadimefon, simeconazole, oxpoconazole fumarate, prothioconazole, bupirimate, spiroxamine, metiram, dodine, anilazine, chlozolinate, oxycarboxin, ethaboxam, iprovalicarb, pyrazophos, fluoroimide, diflumetorim, fenhexamid, famoxadone, fenamidone, cyazofamid, zoxamide, cyflufenamid, boscalid, benthiavalicarb-isopropyl, picoxystrobin, pyraclostrobin, fluoxastrobin and dimoxystrobin;

[2] The composition for preventing plant diseases as described in [1], wherein the Component II is added in the amount of from 0.01 weight part to 50 weight parts based on 1 weight part of the Component I; and

[3] A method for preventing plant diseases, wherein the composition for preventing plant diseases as described in [1] or [2] is applied to the habitation environment of plant pathogens.

By using a composition for preventing plant diseases and a method for preventing the diseases of the present invention as control means, it is possible to exhibit a synergic control effect which is not expected with a single active ingredient against various plant pathogens containing fungi having chemical resistance to existing active ingredients. Furthermore, it is possible to reduce the dosage of the active ingredient (compound) to plant environment, and phytotoxicity suffering does never occur to plants. Further, the composition compound for preventing plant diseases of the present invention contains 2 kinds or more of components having different skeletons or different actions so that it is possible to provide a control means with low possibility of appearance of fungi having chemical resistance.

BEST MODE FOR CARRYING OUT THE INVENTION

The present invention will be described in more detail below.

The composition for preventing plant diseases of the present invention contains Components I and II as active ingredients.

The Component I is (RS)—N-[2-(1,3-dimethylbutyl)thiophen-3-yl]-1-methyl-3-tri fluoromethyl-1H-pyrazole-4-carboxamide (a common name: penthiopyrad (currently applied for ISO)).

The Component II is one or more compounds selected form a group consisting of tetraconazole, flutriafol, imibenconazole, triadimefon, simeconazole, oxpoconazole fumarate, prothioconazole, bupirimate, spiroxamine, metiram, dodine, anilazine, chlozolinate, oxycarboxin, ethaboxam, iprovalicarb, pyrazophos, fluoroimide, diflumetorim, fenhexamid, famoxadone, fenamidone, cyazofamid, zoxamide, cyflufenamid, boscalid, benthiavalicarb-isopropyl, picoxystrobin, pyraclostrobin, fluoxastrobin and dimoxystrobin.

Compounds of the Component II have been known to exhibit a control effect against various plant diseases. The following are common names (in English) of the Component II and related pages as described in The Pesticide Manual, Vol. 13, published by British Crop Protection Council in 2003. In related pages are described various features of chemicals.

1) Tetraconazole, pp. 945 to 946
2) Flutriafol, pp. 487 to 488
3) Imibenconazole, pp. 561 to 562
4) Triadimefon, pp. 986 to 987
5) Simeconazole, pp. 892 to 893
6) Oxpoconazole fumarate, p. 735
7) Prothioconazole, pp. 837 to 838
8) Bupirimate, pp. 116 to 117
9) Spiroxamine, pp. 902 to 903
10) Metiram, pp. 666 to 667
11) Dodine, pp. 356 to 357
12) Anilazine, p. 1042
13) Chlozolinate, pp. 179 to 180
14) Oxycarboxin, p. 736
15) Ethaboxam, p. 374
16) Iprovalicarb, pp. 580 to 581
17) Pyrazophos, pp. 845 to 846
18) Fluoroimide, p. 467
19) Diflumetorim, p. 313
20) Fenhexamid, pp. 408 to 409
21) Famoxadone, pp. 394 to 395
22) Fenamidone, pp. 397 to 398
23) Cyazofamid, pp. 217 to 218
24) Zoxamide, pp. 1035 to 1036
25) Cyflufenamid, p. 225
26) Boscalid, p. 104
27) Benthiavalicarb-isopropyl, p. 79
28) Picoxystrobin, pp. 786 to 787
29) Pyraclostrobin, pp. 842 to 843
30) Fluoxastrobin, pp. 468 to 469
31) Dimoxystrobin, p. 329

The composition for preventing plant diseases of the present invention achieves a synergic effect as compared to a single use of each of active ingredients (Component I or Component II).

The preferred range of the composition for preventing plant diseases according to the present invention is different depending on its formulations, respectively. The penthiopyrad of the Component I is generally contained in the range of 0.01 weight part to 80 weight parts in 100 weight parts of the composition. In the composition for preventing plant diseases of the present invention, the mixture ratio of penthiopyrad of the Component I to a compound of the Component II is not particularly restricted. The compound of the Component II is usually contained in the range of 0.01 weight part to 50 weight parts, preferably in the range of 0.5 weight part to 50 weight parts, more preferably in the range of 0.5 weight part to 30 weight parts, and further preferably in the range of 1 weight part of 20 weight parts based on 1 weight part of the compound of the Component I.

A composition comprising at the same time Components I and II is included in the composition for preventing plant diseases of the present invention. In addition to that, a case where a composition comprising Component I and a composition comprising Component II are treated to the habitation environment of plant pathogens almost at the same time is also included in the scope of the present invention.

Furthermore, the composition for preventing plant diseases of the present invention can be prepared as a composition containing a compound of Component I and a compound of Component II at a high concentration. The high-concentration composition can be diluted with water and used as a liquid for dispersion. Furthermore, the composition for preventing plant diseases according to the present invention can be prepared as a mixture by mixing a composition containing the Component I at a high concentration and a composition containing the Component II at a high concentration to use. Such a high-concentration composition can be diluted with water and used as a dispersion (a tank mixing method). The composition for preventing plant diseases of the present invention may use an active ingredient as it is to the habitation environment of pathogens to be applied. It is generally blended with an inert liquid carrier, a solid carrier and a surface active agent and used in a usually used formulation form such as dust, wettable powder, flowable formulation, emulsifiable concentrate, granules and other generally accepted formulation forms. Furthermore, if needed for formulation purposes, an adjuvant in addition to the surfactant can be added thereto as well.

The term "carrier" used herein refers to a synthetic or natural, inorganic or organic material which is mixed in order to help the active ingredient reach the site to be treated and make easier storage, transportation and handling of the active ingredient compounds. Both solid and liquid carriers can be used so long as the carriers are commonly used for agricultural and horticultural chemicals. No particular restriction is imposed upon the carriers.

As for the solid carrier, there can be exemplified, for example, clays such as montmorillonite, kaolinite and the like; inorganic substances such as diatomaceous earth, white clay, talc, vermiculite, gypsum, calcium carbonate, silica gel, ammonium sulfate and the like; vegetable organic materials such as soybean flour, sawdust, wheat flour and the like; and urea. Furthermore, in order to improve physical properties, high-dispersion silicic acid or high-dispersion absorbent polymer can also be added. As for the liquid carrier, there can be exemplified, for example, aromatic hydrocarbons such as toluene, xylene, cumene and the like; paraffin hydrocarbons such as kerosene, mineral oil and the like; ketones such as acetone, methyl ethyl ketone, cyclohexanone and the like; ethers such as dioxane, diethylene glycol dimethyl ether and the like; alcohols such as methanol, ethanol, propanol, ethylene glycol and the like; aprotic solvents such as dimethylformamide, dimethyl sulfoxide and the like; and water.

Furthermore, the following various adjuvants can be added singly or in combination according to the object, while taking into account the formulation forms, the site of application, etc. Adjuvants are surface active agents which are commonly used; binders such as lignin sulfonic acid, alginic acid, polyvinyl alcohol, gum Arabic, CMC-sodium and the like; and stabilizers such as phenolic compounds, thiol compounds, higher fatty acid esters and the like as antioxidants, phosphates as pH controllers or sometimes light stabilizers. These adjuvants can be used, when necessary, singly or as a mixture. Further, in order to prevent bacteria and fungi, an industrial bactericide or an agent for preventing of decay can also be added in some cases.

Meanwhile, examples of adjuvants which can be used for purpose of emulsification, dispersion, spreading, wetting, binding and stabilization include anionic surface active agents such as lignin sulfonate, alkylbenzene sulfonate, alkylsulfate ester salt, polyoxyalkylene alkylsulfate, polyoxyalkylene alkylphosphate ester salt and the like; nonionic surface active agents such as polyoxyalkylene alkyl ether, polyoxyalkylene alkyl aryl ether, polyoxyalkylene alkylamine, polyoxyalkylene alkylamide, polyoxyalkylene alkylthioether, polyoxyalkylene fatty acid ester, glycerine fatty acid ester, sorbitan fatty acid ester, polyoxyalkylene sorbitan fatty acid ester, polyoxypropylene polyoxyethylene block copolymer and the like; lubricants such as calcium stearate, wax and the like; stabilizers such as isopropyl hydrogen phosphate and the like; natural or synthetic phospholipids of the cephalin or lecithin series such as phosphatidylethanolamine, phosphatidylserine, phosphatidylglycerol, lysolecithin and the like; and other materials such as methylcellulose, carboxymethylcellulose, casein, gum Arabic and the like. However, the adjuvants are not restricted to the aforementioned components.

In the composition for preventing plant diseases according to the present invention, the total amount of the active ingredient which combines the Component I and the Component II is different depending on the type of formulation. It is usually from 0.01 weight % to 30 weight % for dust formulation, from 0.1 weight % to 80 weight % for wettable powder, from 0.5 weight % to 20 weight % for granule, from 2 weight % to 50 weight % for emulsifiable concentrate, from 1 weight % to 50 weight % for flowable formulation, and from 1 weight % to 80 weight % for dry flowable formulation. It is preferably from 0.05 weight % to 10 weight % for dust formulation, from 5 weight % to 60 weight % for wettable powder, from 5 weight % to 20 weight % for emulsifiable concentrate, from 5 weight % to 50 weight % for flowable formulation, and from 5 weight % to 50 weight % for dry flowable formulation. Further, the content of the adjuvant is from 0 weight % to 80 weight % and the content of the carrier is a quantity obtained by subtracting the total content of the active ingredient compound and the adjuvant from 100 weight %.

As the application methods of the composition for preventing plant diseases of the present invention, there can be exemplified, for example, seed treatment, dipping treatment, nursery bed treatment, foliar application, soil drench, soil incorporation and the like. Various application methods that are usually employed by those skilled in the art can also be cited. The composition of the present invention exhibits a sufficient control effect against plant diseases by any of the above methods.

Furthermore, the application amount and concentration of the composition for preventing plant diseases according to the present invention vary depending on target crops, target diseases, frequency of occurrence of diseases, formulation of the compound, application method, various kinds of environmental conditions and the like. In case the composition of the present invention is treated, the amount of active ingredients is suitably from 50 g/ha to 1,000 g/ha and preferably from 100 g/ha to 500 g/ha. When the wettable powder, flowable formulation or emulsifiable concentrate is treated after diluting with water, the dilution is suitably from 200 times to 20,000 times and preferably from 500 to 5,000 times. Further, when the composition of the present invention is used as a seed disinfectant, the amount of the composition (a mixture of Component I and Component II) is from 0.001 to 50 g per 1 kg of a seed and preferably from 0.01 to 10 g per 1 kg of a seed. The composition of the present invention can, of course, be used as a mixture with agricultural chemicals such as other fungicides, insecticides, acaricides, nematicides, herbicides, plant growth regulators and the like, soil conditioners or fertilizer materials and can also be obtained as a mixed formation with these chemicals.

The composition and the prevention method according to the present invention are effective against the following species of plant diseases. Diseases and pathogens which are the targets of the present invention to control are specifically illustrated below.

Concrete examples thereof include rice diseases such as blast (*Pyricularia oryzae*), sheath blight (*Rhizoctonia solani*), helminthosporium leaf spot (*Cochliobolus miyabeanus*) and "bakanae" disease (*Gibberela fujikuroi*); wheat diseases such as powdery mildew (*Erysiphe graminis* f. sp. *hordei*; f. sp. *tritici*), rust (*Pucinia striiformis; P. graminis; P. recondita; P. hordei*), leaf spot (*Pyrenophora graminea*), net blotch (*Pyrenophora teres*), fusarium blight (*Gibberella zeae*), snow blight (*Typhula* sp.; *Micronectriella nivalis*), loose smut (*Ustilago tritici; U. nuda*), bunt (*Tilletia caries*), eye spot (*Pseudocercosporella herpotrichoides*), foot-rot (*Rhizoctonia cerealis*), rhynchosporium leaf blotch (*Rhynchosporium secalis*), septoria leaf blotch (*Septoria tritici*) and glume blotch (*Leptosphaeria nodorum*); kidney beans, cucumber, tomato, strawberry, grape, potato, soybean, cabbage, Japanese eggplant and lettuce diseases such as gray mold (*Botrytis cinerea*); grape diseases such as downy mildew (*Plasmopara viticola*), rust (*Phakopsora ampelopsidis*), powdery mildew (*Uncinula necator*), anthracnose (*Elsinoe ampelina*) and ripe rot (*Glomerella cingulata*); apple diseases such as powdery mildew (*Podosphaera leucotricha*), scab (*Venturia inaequalis*), alternaria leaf spot (*Alternaria mali*), rust (*Gymnosporangium yamadae*), blossom blight (*Scleroinia mali*) and *Valsa* canker (*Valsa mali*); pear diseases such as black spot (*Alternaria kikuchiana*), scab (*Venturia nashicola*), rust (*Gymnosporangium haraeanum*) and physalospora canker (*Physalospora piricola*); peach diseases such as brown rot (*Sclerotinia cinerea*), scab (*Cladosporium carpophilum*) and phomopsis rot (*Phomopsis* sp.) persimmon diseases such as anthracnose (*Gloeosporium kaki*), angular leaf spot (*Cercoapora kaki; Mycosphaerella nawae*) and powdery mildew (*Phyllactinia kakikora*); cucumber diseases such as downy mildew (*Pseudoperonospora cubensis*); Cucurbitaceae family diseases such as damping-off (*Rizoctonia solani*), powdery mildew (*Sphaerotheca fuliginea*), anthracnose (*Colletotrichum lagenarium*) and gummy stem blight (*Mycosphaerella melonis*); tomato diseases such as early blight (*Alternaria solani*), leaf mold (*Cladosporium fulvam*) and late blight (*Phytophthora infestans*); eggplant diseases such as powdery mildew (*Erysiphe cichoraceorum*) and leaf mold (*Mycovellosiella nattrassii*); cruciferous vegetable diseases such as alternaria leaf spot (*Alternaria japonica*), white spot (*Cercosporella barassicae*), clubroot (*Plasmodiophora brassicae*) and black leg (*Phoma lingam*); leek diseases such as rust (*Puccinia allii*) and alternaria leaf spot (*Alternaria porri*); soybean diseases such as purple speck (*Cercospora kikuchii*), sphaceloma scab (*Elsinoe glycines*) and pod and stem blight (*Diaporthe phaseolorum*); kidney bean diseases such as anthracnose (*Colletotrichum lindemuthianum*); peanut diseases such as leaf spot (*Mycosphaerella berkeleyi*) and brown leaf spot (*Cercospora arachidicola*); pea diseases such as powdery mildew (*Erysiphe pisi*) and downy mildew (*Peronospora pisi*) potato diseases such as early blight (*Alternaria solani*), black scurf (*Rhizoctonia solani*) and late blight (*Phytophthora infestans*); broad bean diseases such as downy mildew (*Peronospora viciae*) and phytophthora rot (*Phytophthora nicotianae*); tea diseases such as net blister blight (*Exobasidium reticulatum*), white scab (*Elsinoe leucospila*) and anthracnose (*Colletotrichum theae-sinensis*); tobacco diseases such as brown spot (*Alternaria longipes*), powdery mildew (*Erysiphe cichoracearum*), anthracnose (*Colletotrichum tabacum*) and black shank (*Phytophthora parasitica*); beat diseases such as cercospora leaf spot (*Cercospora beticola*) rose diseases such as black spot (*Diplocarpon rosae*), powdery mildew (*Sphaerotheca pannosa*) and phytophthora disease (*Phytophthora megasperma*); chrysanthemum diseases such as leaf blotch (*Septoria chrysanthemi-indici*) and rust (*Puccinia horiana*); strawberry diseases such as powdery mildew (*Sphaerotheca humuli*) and phytophthora rot (*Phytophthora nicotianae*); kidney bean, cucumber, tomato, potato, grape, strawberry, soybean, cabbage, Japanese eggplant and lettuce diseases such as *sclerotinia* rot (*Sclerotinia sclerotiorum*) citrus diseases such as melanose (*Diaporthe citri*); carrot diseases such as leaf bright (*Alternaria dauci*), and the like.

EXAMPLES

The present invention is now more specifically illustrated below with reference to Examples. However, the present invention is not limited to these Examples. Incidentally, all combination part numbers of each component as described in Formulation Examples hereinafter indicate weight parts.

Example A

Formulation Example a

Formulation Example a1 Wettable Powder Containing Components I and II

A wettable powder was obtained by grinding and mixing the total 100 parts comprising 5 parts of penthiopyrad of Component I, Component II (any one of the compounds described below and the amount used (parts) thereof), 5 parts of sodium lignin sulfonate, 10 parts of sodium alkylbenzene sulfonate, 10 parts of white carbon, and rest of parts of diatomaceous earth or clay.

In Formulation Example a1, Component II and the amount used (parts) thereof were respectively 5 parts of tetraconazole, 5 parts of flutriafol, 5 parts of imibenconazole, 5 parts of triadimefon, 5 parts of simeconazole, 5 parts of oxpoconazole fumarate, 5 parts of prothioconazole, 10 parts of bupirimate, 25 parts of spiroxamine, 25 parts of metiram, 25 parts of dodine, 25 parts of anilazine, 20 parts of chlozolinate, 10 parts of oxycarboxin, 5 parts of ethaboxam, 2.5 parts of iprovalicarb, 10 parts of pyrazophos, 15 parts of fluoroimide, 5 parts of diflumetorim, 10 parts of fenhexamid, 10 parts of famoxadone, 5 parts of fenamidone, 5 parts of cyazofamid, 5 parts of zoxamide, 2.5 parts of cyflufenamid, 10 parts of boscalid, and 2. 5 parts of benthiavalicarb-isopropyl.

Comparative Formulation Example a 1-2

Wettable Powder Containing Component I
Formulation Containing Only Penthiopyrad

A wettable powder was obtained by grinding and mixing the total 100 parts comprising 10 parts of penthiopyrad, 5 parts of sodium lignin sulfonate, 10 parts of sodium alkylbenzene sulfonate, 10 parts of white carbon, and rest of parts of diatomaceous earth or clay.

Comparative Formulation Example a 1-3

Wettable Powder Containing Component II
Formulation Containing Only One of Component II A wettable powder was obtained by grinding and mixing the total 100 parts comprising Component II (any one of the compounds described below and its part number), 5 parts of sodium lignin sulfonate, 10 parts of sodium alkylbenzene sulfonate, 10 parts of white carbon, and rest of parts of diatomaceous earth or clay.

In Comparative Formulation Example a 1-3, Component II and the part number thereof were respectively 10 parts of tetraconazole, 10 parts of flutriafol, 10 parts of imibenconazole, 10 parts of triadimefon, 10 parts of simeconazole, 10 parts of oxpoconazole fumarate, 10 parts of prothioconazole, 20 parts of bupirimate, 50 parts of spiroxamine, 50 parts of metiram, 50 parts of dodine, 50 parts of anilazine, 40 parts of chlozolinate, 20 parts of oxycarboxin, 10 parts of ethaboxam, 5 parts of iprovalicarb, 20 parts of pyrazophos, 30 parts of fluoroimide, 10 parts of diflumetorim, 20 parts of fenhexamid, 20 parts of famoxadone, 10 parts of fenamidone, 10 parts of cyazofamid, 10 parts of zoxamide, 5 parts of cyflufenamid, 20 parts of boscalid, and 5 parts of benthiavalicarb-isopropyl.

Test Examples on Disease Control

Hereinafter, the results from Test Examples on disease control are specifically illustrated. Further, in each Table, an alphabet P indicates penthiopyrad of Component I. Furthermore, in all of the Test Examples as described below, a synergic effect was recognized and no symptom of phytotoxicity suffering to the plant was confirmed, as compared to the single use of an active ingredient.

Test Example 1

Control Test on Powdery Mildew of Cucumbers EBI Resistant Strain

In a greenhouse, two seedlings of cucumbers (cultivar: sagami-hanjiro) were planted in a plastic pot having a diameter of 7.5 cm and grown until 1.5 leaf stage. The wettable powder which was prepared according to Formulation Example a1 was diluted with water to the prescribed concentration and treated by 50 ml portions per four pots using a spray gun. After a liquid chemical was dried, the leaves of cucumbers which were previously arranged to be damaged by the pathogen were uniformly wiped with powdery mildew pathogen (EBI resistant strain) thereon using a paintbrush for inoculation. After the inoculation, the plastic pot was put into a homoiothermal chamber (20° C. to 25° C.) in the greenhouse and taken out therefrom after 14 days have passed to carry out the examination. The area ratio occupied by lesion per one leaf of cucumber was examined in accordance with the following severity index. Furthermore, the control value was calculated according to the following equation from the average severity of each plot. At the same time, the same tests were carried for Comparative Formulation Examples (formulation containing only one of active ingredient) such as Formulation Example a 1-2 and Formulation Example a 1-3. The results are shown in Table 1.

| Disease severity | 0: No lesion |
|---|---|
| | 1: Lesion area was not more than 5% |
| | 2: Lesion area was 6-25% |
| | 3: Lesion area was 26-50% |
| | 4: Lesion area was not less than 51% |

The mean value of each treated plot and untreated plot was defined as disease severity. The control value was calculated in the following manner.

Control Value=(1−disease severity in the treated plot/disease severity in the untreated plot)×100

TABLE 1

Table 1 Control Test on Powdery Mildew of Cucumbers

| Active Ingredient in the Formulation | Treated Concentration (ppm) | Control Value |
|---|---|---|
| P + tetraconazole | 5 + 5 | 89 |
| P + triadimefon | 5 + 5 | 88 |
| P + bupirimate | 5 + 10 | 90 |
| P + cyflufenamid | 5 + 2.5 | 98 |
| Tetraconazole | 10 | 34 |
| Triadimefon | 10 | 29 |
| Bupirimate | 20 | 45 |
| Cyflufenamid | 5 | 66 |
| P (penthiopyrad) | 10 | 68 |

Test Example 2

Control Test on Powdery Mildew of Wheat EBI Resistant

In a greenhouse, wheat (cultivar: chihoku, about 20 stocks/pot) was grown in a plastic pot having a diameter of 7.5 cm until the 1.5 leaf stage. The wettable powder which was prepared according to Formulation Example a1 was diluted to the prescribed concentration and treated by 50 ml portions per three pots using a spray gun. At the same time, the wettable powders according to Comparative Formulation Examples (formulation containing only one of active ingredient) such as Formulation Example a 1-2 and Formulation Example a 1-3 were treated in the same manner.

After a liquid chemical was dried, powdery mildew pathogen (EBI resistant strain) of wheat was inoculated on the leaf surface. After the inoculation, the plastic pot was put into an artificial weather chamber at a temperature of from 17° C. to 21° C. and taken out therefrom after 9 days have passed to carry out the examination. The area ratio occupied by lesion per one leaf of wheat was examined in the same manner as in Test Example 1. The control value was calculated in the same manner as well. The results are shown in Table 2.

TABLE 2

Table 2 Control Test on Powdery Mildew of Wheat

| Active Ingredient in the Formulation | Treated Concentration (ppm) | Control Value |
|---|---|---|
| P + flutriafol | 5 + 5 | 85 |
| P + prothioconazole | 5 + 5 | 85 |
| P + spiroxamine | 5 + 25 | 94 |
| P + pyrazophos | 5 + 10 | 92 |
| P + diflumetorim | 5 + 5 | 93 |
| Flutriafol | 10 | 55 |
| Prothioconazole | 10 | 42 |
| Spiroxamine | 50 | 65 |
| Pyrazophos | 20 | 65 |
| Diflumetorim | 10 | 65 |
| P (penthiopyrad) | 10 | 54 |

Test Example 3

Control Test on Late Blight of Tomatoes Phenylamide-Resistant Strain

In a greenhouse, tomatoes (cultivar: sekai-ichi) were grown in a plastic pot having a diameter of 7.5 cm until the 5 leaf stage. The wettable powder which was prepared according to Formulation Example a1 was diluted with water to the prescribed concentration and treated by 50 ml portions per four pots using a spray gun. At the same time, the wettable powders according to Comparative Formulation Examples (formulation containing only one of active ingredient) such as Formulation Example a 1-2 and Formulation Example a 1-3 were treated in the same manner. After the liquid chemical treated on the plants was dried, a suspension of phenylamide-resistant strain (zoospore+zoosporangia) was inoculated. After the inoculation, the pot was put into an artificial weather control chamber (16° C. to 20° C.) in the greenhouse and taken out therefrom after 5 days have passed to carry out the examination. The diseased leaflet ratio, that is, the ratio of diseased leaflets per the whole leaflets of tomatoes was examined. The mean value of each treated plot and untreated plot was defined as the diseased leaflet ratio. The control value was calculated in the following manner. The results are shown in Table 3.

Control Value=(1−diseased leaflet ratio in the treated plot/diseased leaflet ratio in the untreated plot)× 100

TABLE 3

Table 3 Control Test on Late Blight of Tomatoes

| Active Ingredient in the Formulation | Treated Concentration (ppm) | Control Value |
|---|---|---|
| P + metiram | 5 + 25 | 80 |
| P + ethaboxam | 5 + 5 | 88 |
| P + iprovalicarb | 5 + 2.5 | 90 |
| P + famoxadone | 5 + 10 | 80 |
| P + fenamidone | 5 + 5 | 86 |
| P + cyazofamid | 5 + 5 | 90 |
| P + zoxamide | 5 + 5 | 82 |
| P + benthiavalicarb-isopropyl | 5 + 2.5 | 95 |
| Metiram | 50 | 56 |
| Ethaboxam | 10 | 62 |
| Iprovalicarb | 5 | 70 |
| Famoxadone | 20 | 62 |
| Fenamidone | 10 | 58 |
| Cyazofamid | 10 | 70 |
| Zoxamide | 10 | 60 |
| Benthiavalicarb-isopropyl | 5 | 70 |
| P (penthiopyrad) | 10 | 20 |

Test Example 4

Control Test on Gray Mold of Tomato at its Flowering Stage Gray Mold: RS Strain

In a greenhouse, tomatoes (cultivar: House-Momotaro) were grown in a 1/5000a Wagner's pot until the flowering stage. The wettable powder which was prepared according to Formulation Example a1 was diluted to the prescribed concentration and treated by 150 ml portions per four pots using a spray gun twice at an interval of one week. At the same time, the wettable powders according to Comparative Formulation Examples (formulation containing only one of active ingredient) such as Formulation Example a 1-2 and Formulation Example a 1-3 were treated in the same manner. Conidiospore suspension was prepared from gray mold fungus (MBC resistant, dicarboximide-based chemical sensitive: RS strain) which was previously cultured on a PDA medium. After one day from the treatment of the chemical, a conidiospore suspension containing the culture fluid was spray-inoculated mainly over the flower part twice at an interval of one week. After the inoculation, the Wagner's pot was put into a moist chamber at a temperature of from 15° C. to 30° C. under humidity of not less than 90% in the greenhouse and taken out therefrom after 7 days have passed to carry out the examination. Diseased fruit ratio (the ratio of diseased young fruits occupied by the total number of tomato young fruits) of each pot was examined. The mean of diseased fruit ratio of each treated plot was obtained and the control value was calculated in the following manner. The results are shown in Table 4.

Control Value=(1−diseased fruit ratio in the treated plot/diseased fruit ratio in the untreated plot)×100

TABLE 4

Table 4 Control Test on Gray Mold of Tomato at its Flowering Stage

| Active Ingredient in the Formulation | Treated Concentration (ppm) | Control Value |
|---|---|---|
| P + anilazine | 5 + 25 | 92 |
| P + chlozolinate | 5 + 20 | 83 |
| P + fenhexamid | 5 + 10 | 95 |
| P + boscalid | 5 + 10 | 90 |
| Anilazine | 50 | 40 |
| Chlozolinate | 40 | 42 |
| Fenhexamid | 20 | 55 |
| Boscalid | 20 | 48 |
| P (penthiopyrad) | 10 | 56 |

Test Example 5

Control Test on *Alternaria* Leaf Spot of Apples

In a greenhouse, apples (cultivar: ourin) were grown in a plastic pot having a diameter of 7.5 cm until the 15 leaf stage or more. The wettable powder which was prepared according to Formulation Example a1 was diluted with water to the prescribed concentration and treated by 100 ml portions per three pots using a handy spray. At the same time, the wettable powders according to Comparative Formulation Examples (formulation containing only one of active ingredient) such as Formulation Example a 1-2 and Formulation Example a 1-3 were treated in the same manner. After a liquid chemical was dried, 10 trees attacked by *alternaria* leaf spot pathogen of apples which were previously arranged to be diseased were placed on the windward side and apples of test pots placed on the leeward side by wind of an air conditioner were wind-inoculated. After the inoculation, the test pots were put into a homoiothermal chamber (20° C. to 25° C.) in the greenhouse and taken out therefrom after 20 days have passed to carry out the examination. The area ratio occupied by lesion per one leaf of an apple was examined according to the same index as in Test Example 1. The control value was calculated from the average of the disease severity of each plot in the same manner as in Test Example 1. The results are shown in Table 5.

TABLE 5

Table 5 Control Test on Alternaria Leaf Spot of Apples

| Active Ingredient in the Formulation | Treated Concentration (ppm) | Control Value |
|---|---|---|
| P + imibenconazole | 5 + 5 | 92 |
| P + oxpoconazole fumarate | 5 + 5 | 94 |
| P + dodine | 5 + 25 | 80 |

TABLE 5-continued

Table 5 Control Test on Alternaria Leaf Spot of Apples

| Active Ingredient in the Formulation | Treated Concentration (ppm) | Control Value |
|---|---|---|
| P + fluoroimide | 5 + 15 | 90 |
| Imibenconazole | 10 | 42 |
| Oxpoconazole fumarate | 10 | 46 |
| Dodine | 50 | 44 |
| Fluoroimide | 30 | 45 |
| P (penthiopyrad) | 10 | 50 |

Test Example 6

Control Test on Brown Patch of Turf Grass

In a greenhouse, the soil that is mixed with brown patch pathogen cultured by wheat bran was filled in a lower layer part of a plastic pot having a diameter of 7.5 cm and in 4 cm of an upper layer part, the grass (cultivar: Pentocross) which was previously grown was torn off with soil and transplanted. After three days from the transplantation, the wettable powder which was prepared according to Formulation Example a1 was diluted with water to the prescribed concentration, an aqueous solution of chemicals or the like was soaked into soil by 40 ml per pot, and then was kept for 20 days at 20° C. to 30° C. Then, the area ratio of brown patch pathogen-attacked portion to the whole surface of the pot was examined according to the same index as in Test Example 1. The control value was calculated in the same manner as well. At the same time, the same tests were carried for Comparative Formulation Examples (formulation containing only one of active ingredient) such as Formulation Example a 1-2 and Formulation Example a 1-3. The results are shown in Table 6.

TABLE 6

Table 6 Control Test on Brown Patch of Grass

| Active Ingredient in the Formulation | Treated Concentration (ppm) | Control Value |
|---|---|---|
| P + simeconazole | 5 + 5 | 92 |
| P + oxycarboxin | 5 + 10 | 85 |
| Simeconazole | 10 | 48 |
| Oxycarboxin | 20 | 42 |
| P (penthiopyrad) | 10 | 53 |

In all Test Examples as illustrated above in Example A, a composition for preventing plant diseases containing penthiopyrad of Component I and a prescribed Component II was recognized to exhibit a synergic control effect and no symptom of phytotoxicity suffering to the plant was recognized, as compared to a composition for preventing plant diseases containing a single active ingredient.

Example B

Formulation Example b

Formulation Example b1 Wettable Powder Containing Components I and II

A wettable powder was obtained by grinding and mixing the total 100 parts comprising 5 parts of penthiopyrad of Component I, Component II (any one of the compounds described below and the amount used (parts) thereof), 5 parts of sodium lignin sulfonate, 10 parts of sodium alkylbenzene sulfonate, 10 parts of white carbon, and rest of parts of diatomaceous earth or clay.

In Formulation Example b1, Components II and the amount used (parts) thereof were respectively 7.5 parts of picoxystrobin, 2.5 parts of pyraclostrobin, 5 parts of fluoxastrobin and 7.5 parts of dimoxystrobin.

Comparative Formulation Example b 1-2

Wettable Powder Containing Component I
Formulation Containing Only Penthiopyrad

A wettable powder was obtained by grinding and mixing the total 100 parts comprising 10 parts of penthiopyrad, 5 parts of sodium lignin sulfonate, 10 parts of sodium alkylbenzene sulfonate, 10 parts of white carbon, and rest of parts of diatomaceous earth or clay.

Comparative Formulation Example b 1-3

Wettable Powder Containing Component II
Formulation Containing Only One of Component II A wettable powder was obtained by grinding and mixing the total 100 parts comprising Component II (any one of the compounds described below and the amount used (parts) thereof), 5 parts of sodium lignin sulfonate, 10 parts of sodium alkylbenzene sulfonate, 10 parts of white carbon, and rest of parts of diatomaceous earth or clay.

In Comparative Formulation Example b 1-3, Components II and the amount used (parts) thereof were respectively 15 parts of picoxystrobin, 5 parts of pyraclostrobin, 10 parts of fluoxastrobin and 15 parts of dimoxystrobin.

Test Examples on Disease Control

Hereinafter, the results from Test Examples on disease control are specifically illustrated. Further, in each Table, an alphabet P indicates penthiopyrad of Component I. Test Examples were carried out in the same manner as in Test Examples 1 to 3 in Example A. The results from Test Example 1 were shown in Table 7, the results from Test Example 2 in Table 8, and the results from Test Example 3 in Table 9.

TABLE 7

Table 7 Control Test on Powdery Mildew of Cucumbers

| Active Ingredient in the Formulation | Treated Concentration (ppm) | Control Value |
| --- | --- | --- |
| P + dimoxystrobin | 5 + 7.5 | 98 |
| Dimoxystrobin | 15 | 60 |
| P (penthiopyrad) | 10 | 68 |

TABLE 8

Control Test on Powdery Mildew of Wheat

| Active Ingredient in the Formulation | Treated Concentration (ppm) | Control Value |
| --- | --- | --- |
| P + picoxystrobin | 5 + 7.5 | 98 |
| P + fluoxastrobin | 5 + 5 | 98 |
| Picoxystrobin | 15 | 66 |
| Fluoxastrobin | 10 | 68 |
| P (penthiopyrad) | 10 | 54 |

TABLE 9

Table 9 Control Test on Late Blight of Tomatoes

| Active Ingredient in the Formulation | Treated Concentration (ppm) | Control Value |
| --- | --- | --- |
| P + pyraclostrobin | 5 + 2.5 | 92 |
| Pyraclostrobin | 5 | 62 |
| P (penthiopyrad) | 10 | 20 |

In all Test Examples as illustrated above in Example B, a composition for preventing plant diseases containing penthiopyrad of Component I and a prescribed Component II was recognized to exhibit a synergic control effect and no symptom of phytotoxicity suffering to the plant was recognized, as compared to a composition for preventing plant diseases containing a single active ingredient.

The invention claimed is:

1. A composition for controlling plant diseases comprising Components I and II as active ingredients, wherein the Component I is (RS)—N-[2-(1,3-dimethylbutyl)thiophen-3-yl]-1-methyl-3-trifluoromethyl-1H-pyrazole-4-carboxamide, and the Component II is famoxadone, picoxystrobin, pyraclostrobin, fluoxastrobin or dimoxystrobin, wherein the Component II is added in an amount of from 0.5 weight part to 5 weight parts based on 1 weight part of the Component I.

2. A method for controlling plant diseases, wherein the composition for preventing plant diseases as described in claim 1 is applied to the habitation environment of plant pathogens.

* * * * *